United States Patent [19]
Johnson

[11] Patent Number: 5,140,707
[45] Date of Patent: Aug. 25, 1992

[54] WELDER'S SAFETY HELMET

[76] Inventor: Gary L. Johnson, Box 77, Hugheston, W. Va. 25110

[21] Appl. No.: 599,063

[22] Filed: Oct. 17, 1990

[51] Int. Cl.⁵ .............................................. A61F 9/06
[52] U.S. Cl. ......................................................... 2/8
[58] Field of Search ........................................ 2/7, 8, 9

[56] References Cited
U.S. PATENT DOCUMENTS

| | | | |
|---|---|---|---|
| 2,017,059 | 10/1935 | Gingg | 2/8 |
| 2,105,071 | 1/1938 | Bowers | 2/8 |
| 2,251,194 | 7/1941 | Malcom | 2/8 |
| 2,384,765 | 9/1945 | O'Reilly | 2/8 |
| 2,411,224 | 11/1946 | O'Reilly | 2/8 |
| 2,590,526 | 3/1952 | Evans | 2/8 |
| 2,719,972 | 10/1955 | Kelly | 2/8 |
| 3,251,065 | 5/1966 | Caldwell | 2/8 |
| 3,257,667 | 6/1966 | Anderson | 2/8 |
| 4,109,132 | 8/1978 | Butoi | 2/8 |
| 4,193,132 | 3/1980 | Peterson | 2/8 |
| 4,706,301 | 11/1987 | Page | 2/8 |
| 4,875,235 | 10/1989 | Kuhlman | 2/8 |

Primary Examiner—Werner H. Schroeder
Assistant Examiner—Michael A. Neas
Attorney, Agent, or Firm—Renner, Kenner, Greive, Bobak, Taylor & Weber

[57] ABSTRACT

A welder's safety helmet has a face portion (11) and an observation aperture (16). The face portion (11) supports a lens assembly (20). The lens assembly (20) includes a shroud (21) and a first lens frame (22) having a first lens (31) mounted therein. The shroud (21) substantially surrounds the observation aperture (16). The first lens frame (22) is operable between an open and a closed position via a hinge mechanism (23). In the closed position, a spacer member (40) contacts the shroud (21) and thus effectively blocks all light from being transmitted to the wearer's field of view, other than the desirable transmission through first lens (31).

7 Claims, 2 Drawing Sheets

WELDER'S SAFETY HELMET

TECHNICAL FIELD

The present invention generally relates to a welder's safety helmet. More particularly, the present invention relates to a welder's safety helmet having multiple lenses. Specifically, the present invention relates to a welder's safety helmet having a lens assembly providing improved impedance of light into the user's field of view and an internal lens locking system.

BACKGROUND OF THE INVENTION

It is known in the welding art to employ a safety helmet having a face portion. Further, it is known in the art to provide an observation aperture in the face portion in order to allow the wearer to observe his work during a welding procedure. The helmet protects the wearer from sparks and flying debris which may be encountered during such a procedure.

In addition to functioning as a "window" for the wearer to observe his work, safety glass is also employed in welder's safety helmets in order to protect the wearer from the often intense and potentially hazardous light or electromagnetic radiation emissions associated with welding. Such emissions vary in wavelength from ultra violet, to the visible spectrum, to infra red, depending upon the nature of the welding equipment employed. Safety glass is used to block all but a minute amount of these intense emissions, thus allowing the welder to focus directly upon the welding task, without fear of eye damage.

Because of the nature of the glass employed, nearly one hundred percent of visible spectrum light is blocked. Thus, a person wearing a welder's safety helmet, and looking through the safety glass, would be essentially blinded to all but very intense light emissions. The welder's work site is often a potentially hazardous location on its own. At such a site, a "blinded" workman increases the potential for a hazard. Therefore, it is a common practice for welder's to orient themselves at their work site, including positioning their hands and equipment for welding, before moving the safety glass in front of their eyes.

It is also known in the art to provide a safety helmet with a light radiation blocking lens hingedly connected to the safety helmet, and a clear glass lens affixed in front of the observation aperture. Thus, the welder positions himself at the work site, observing his surroundings through the clear glass lens. Immediately prior to beginning to weld, the light radiation blocking lens is pivoted at the hinge to a position in front of the clear glass lens, and welding can then begin.

An example of a welder's helmet employing a hinged safety lens is disclosed in U.S. Pat. No. 2,719,972. As is shown therein, it is known to employ two hinged safety glasses, each for a separate task. For instance, one lens may be of the type employed in welding operations, while the other may be of the type used for cutting operations. Because the light radiation emissions during each procedure is different, different lenses are required for different tasks.

It is known in the art, that during welding operations, light radiation must be prevented from entering the welder's field of view, except that which is permitted to pass through the safety lens. For this reason, welder's safety helmets such as that disclosed in U.S. Pat. No. 2,719,972, often employ a complex series of fastening and securing devices, such as external springs and clamps. As described above, light radiation emissions are a potential hazard, any such emissions which enter the welder's field of view could permanently damage the welder's eyesight.

Welder's safety helmets having one or more hinged safety glass lenses have proven to be beneficial in the welder's art. However, those helmets heretofore known by the inventor have all included external safety lens securing and fastening means. As stated above, U.S. Pat. No. 2,719,972 employs a series of hold-down springs, external to the helmet itself. Further, the safety glass lenses themselves, and the frame structures supporting them, are also positioned externally on the helmet. This positioning exposes the lenses, the lens frames and the securing and fastening means to the potential of being knocked, butted and jarred by surrounding objects. As alluded to above, sites where welding takes place, such as construction sites and the like, are often hazardous places. This is so because there are often exposed support beams, various pieces of equipment and the like. This increases the likelihood that the external securing structures of a welder's helmet will be struck and damaged. Further, in such environments sparks and particles of molten metal are prevalent, posing a threat to exposed springs and clamps in the prior art structures.

A damaged safety lens will potentially be susceptible to light impedance failure. That is, if the frame supporting the safety lens is damaged, light radiation emissions from the welding procedure can enter the welder's field of view, causing sever eye damage.

Therefore, a need exists for a welder's helmet having an interchangeable safety lens structure which will securely position a safety lens over the wearer's field of view; which will effectively prevent light radiation emissions from entering the field of view other than through the safety glass; which will serve to prevent damage to the safety lenses and the structures which impede the entrance of the light radiation emissions; and, which will not require the use of external fastening or securing devices.

DISCLOSURE OF THE INVENTION

It is therefore, an aspect of the present invention to provide a welder's safety helmet.

It is another aspect of the present invention to provide a safety helmet as above, which has interchangeable safety lenses.

It is a further aspect of the present invention to provide a safety helmet as above, which will prevent damage to the safety lenses, the securing and fastening structure therefor, and the structures employed to impede light radiation emissions.

These and other aspects of the present invention, as well as the advantages thereof over existing prior art forms, which will become apparent from the description to follow, are accomplished by the means hereinafter described and claimed.

In general, a welder's helmet according to the present invention has a face portion with an observation aperture therein. A lens assembly is disposed upon the face of the helmet and has a shroud extending therefrom, in a direction away from the face. The shroud substantially surrounds the observation aperture. A first lens frame carries a first lens. The first lens frame is connected via hinge means to the helmet and is operable via the hinge means between an open position away from the observation aperture and a closed position in juxtaposition with the observation aperture. The first lens frame has a spacer member substantially surrounding the first lens. The spacer member is in engagement with the shroud when the lens frame is in the closed position, such that engagement of the spacer member of the first lens frame with the shroud when the first lens frame is in the closed position prevents light from traversing between the spacer member and the shroud and past the face portion. Means are also provided for securing the first lens frame in the closed position.

A preferred welder's safety helmet incorporating the concepts of the present invention is shown by way of example in the accompanying drawings without attempting to show all the various forms and modifications in which the invention might be embodied, the invention being measured by the appended claims and not by the details of the specification.

BRIEF DESCRIPTION OF THE DRAWINGS

FIG. 3 is the cross-sectional side view of the welder's safety helmet of FIG. 2, showing the other of the two safety lenses in position for use.

BEST MODE FOR CARRYING OUT THE INVENTION

Figure 2:
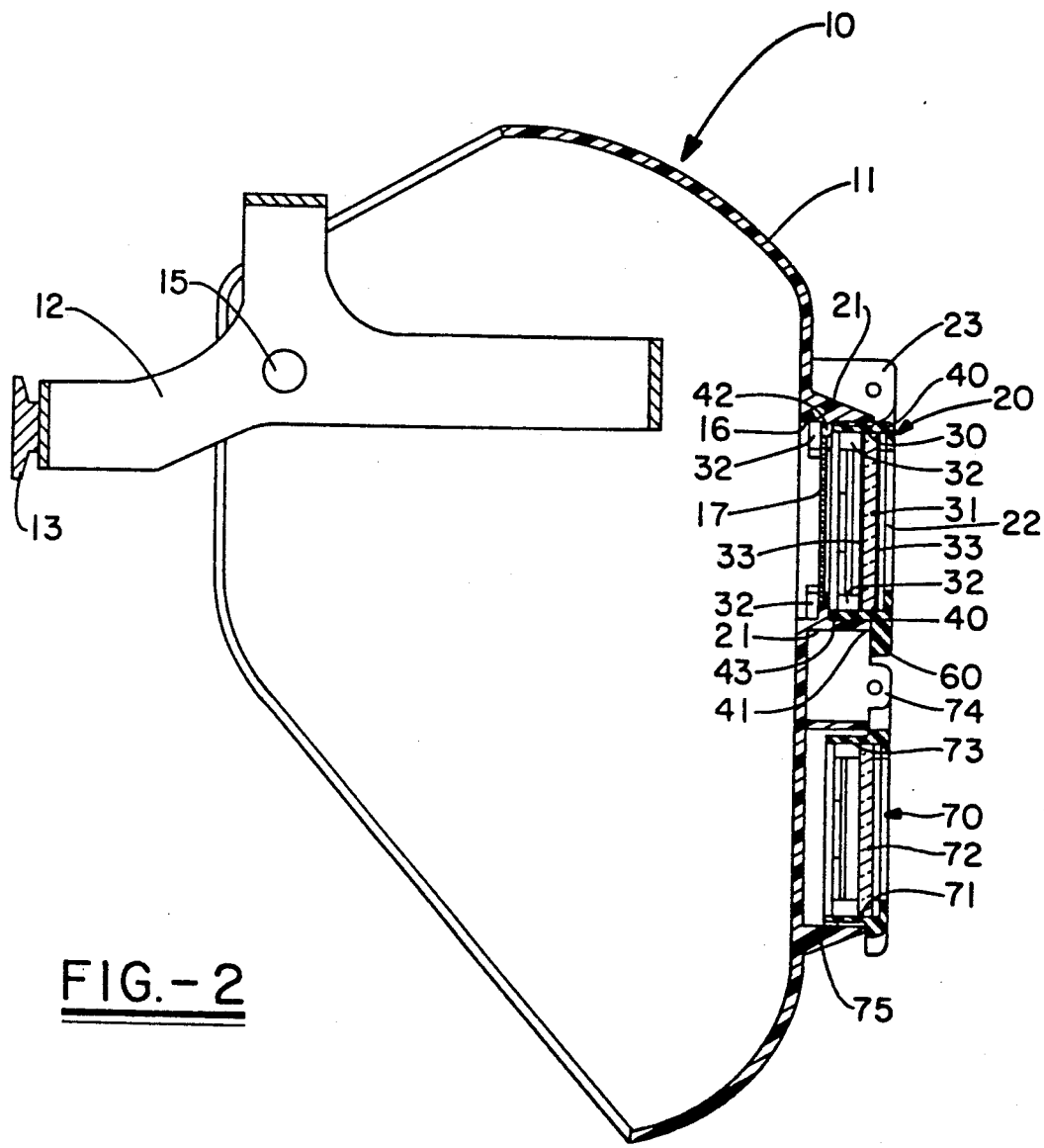
FIG. 2 is a cross-sectional side view of the welder's safety helmet in FIG. 1, showing one of two safety lenses in position for use.

A welder's safety helmet embodying the concepts of the present invention is generally indicated by the numeral 10 on the accompanying drawings. As is known in the art, the helmet 10 includes a face portion 11, and a headband assembly 12 having an adjusting mechanism 13 (FIG. 2). A welder employs the helmet 10 by placing the headband 12 on his head, and adjusting the fit with adjusting mechanism 13. The face portion 11 may be pivoted at a pivot point 15 to a position either in front of or away from the wearer's face, while the headband 12 remains in place.

As is also known in the art, helmet 10 is provided with an observation aperture 16, which may be covered with a clear safety glass 17. Observation aperture 16 allows the welder to observe his work during a welding procedure.

The helmet 10 according to the present invention has a lens assembly generally indicated by the numeral 20 on the accompanying drawings. Lens assembly 20 has a shroud 21 extending therefrom and substantially surrounding observation aperture 16. Shroud 21 extends from lens assembly 20 in a direction away from face portion 11 and away from headband 12. Shroud 21 essentially encloses an area generally in front of observation aperture 16. By "in front of" it is understood to be in a direction away from face portion 11 and away from headband 12, in a manner similar to "in front of" a person's face.

Figure 1:
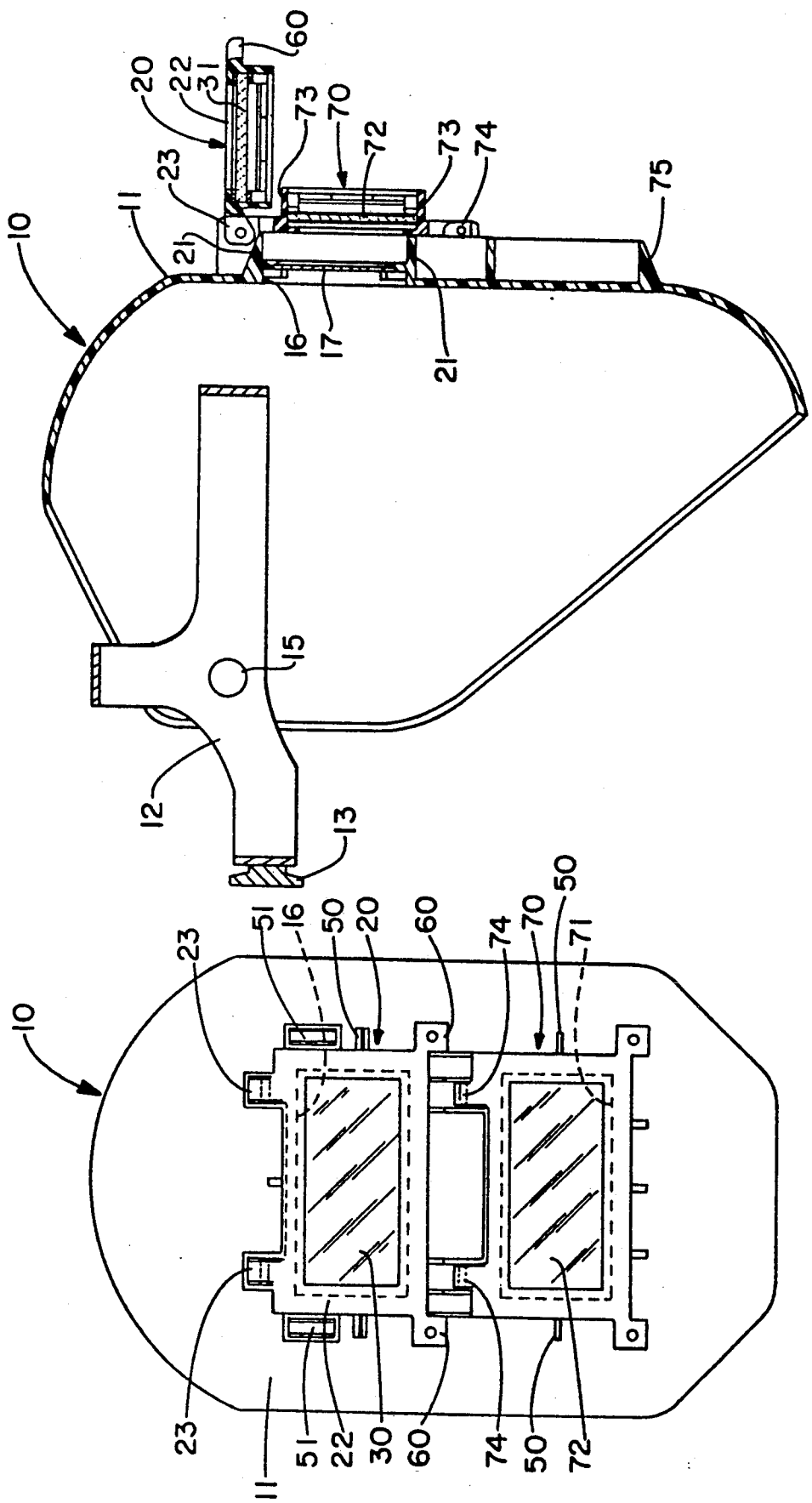
FIG. 1 is a perspective view of a welder's safety helmet embodying the concepts of the present invention.

Lens assembly 20 also includes a first lens frame 22. First lens frame 22 is connected to helmet 10 via a hinge assembly 23. In the embodiment of the invention depicted in FIG. 1, two hinge assemblies 23 are employed. It is to be understood that one or more hinge assemblies 23 are operable in a substantially similar manner, and any number thereof is within the spirit of the present invention.

First lens frame 22 has a first lens aperture 30 into which is mounted a first lens 31 (FIG. 2). First lens aperture 30 is dimensioned to be approximately equal to observation aperture 16, although it may be larger or smaller than observation aperture 16 and still be within the scope of the present invention. First lens 30 may be mounted in numerous ways, including by the use of pressure fingers 32. Further, first lens 31 may be mounted between clear glass safety lenses 33, which may themselves be similar to clear glass safety lens 17 covering observation aperture 16.

First lens 31 may be any type of welding, cutting or other type of safety glass, but preferably is a safety glass used during a welding procedure.

First lens frame 22 is provided with a spacer member 40 which spacer member 40 substantially surrounds first lens aperture 30. First lens 31 then, is substantially mounted within spacer member 40.

First lens frame 22 is operable via hinge assembly 23 between an open and closed position. By "open position" it is meant that first lens frame 22 is in a position away from observation aperture 16. By "closed position" it is meant a position for welding use wherein first lens frame 22 is in juxtaposition with observation aperture 16, and first lens frame aperture 30 covers observation aperture 16. Thus, with first frame 22 in the closed position, a welder wearing helmet 10 would have his direct line of vision being through observation aperture 16 and first lens frame aperture 30, and of course, also through the lenses 17 or 31 which may be mounted therein.

Also, when first lens frame 22 is in the closed position, spacer member 40 fits within shroud 21. In the embodiment depicted in the drawings, spacer member 40 contacts shroud 21 at a spacer member shoulder 41. Further, shroud 21 may be provided with an extension member 42, which contacts an end portion 43 of spacer member 40. Shroud 21 extension member 42 may also be employed to mount safety glass lens 17 covering observation aperture 16. The contact between shroud 22 and spacer member 40 will prevent light radiation emissions from entering between those two elements. Thus, with the first lens frame 22 in the closed position, light can enter the wearer field of view only through the first lens 31. Thus, all light entering the wearer's field of view is effectively filtered.

It is to be appreciated that the contact between spacer member 40 and shroud 21 may be accomplished in numerous ways other than by the contact of shoulder 41 or end portion 43. Any light blocking contact between first frame 22 and shroud 21 is within the scope of the present invention. It is envisioned that spacer member 40 may be a machined metal or polymeric material with exacting dimensions to contact shroud 21 and block light from traversing therebetween. Further, spacer member 40 may be a resilient material such as a rubber or other polymer, which contacts shroud 21, compresses and forms a light blocking fit. One skilled in the art will appreciate that all such structures are within the scope of the present invention.

First frame 22 is secured in the closed position by any of a numerous number of structures. Such structures would include clip and catch structure 50, magnetic elements 51, and others within the scope of the present invention yet not depicted in the drawings, such as bump and detente means. Preferably, clips 50 are provided internally of shroud 21. Another preferred structure includes magnetic elements 51 secured to either face portion 11, shroud 21, spacer member 40, first lens frame 22 or a combination thereof, and acting so as to magnetically attract and urge first lens frame 22 into the closed position. Again, one skilled in the art will appreciate that all such structures are within the scope of the present invention. However, it is preferred that any such structure be positioned within shroud 21 when first lens frame 22 is in the closed position. In this way, the securing means such as clips 50 and/or magnetic elements 51 are protected by shroud 21.

Those skilled in the art will readily appreciate that the first frame 22 may be secured in its open position by any of numerous structures presently known in the art. By way of example, but not limitation, the bump and detente means discussed above can readily be used for this purpose. Additionally, flip frames or spring biased mechanisms as are presently well known and understood in the art can be used for such purpose, the same being shown in prior U.S. Pat. Nos. 2,384,765, 2,411,224, and 2,590,526.

It is to be appreciated that the interaction between first lens frame 22 and shroud 21, as described above, will function so as to prevent the transmission of light other than that which desirably occurs through first lens 31. Further, the same interaction will function to protect the securing structures, i.e. clips 50 and/or magnetic elements 51. Thus, clips 50 and/or magnetic elements 51 are protected from flying sparks and debris, and from the corrosive and potentially corroding environments often encountered at sites where welding occurs, and as were described above.

First lens frame 22 may be provided with knob extensions 60. The wearer would slip a finger under knob extensions 60 in order to maneuver first lens frame between the open and closed position.

Lens assembly 20 may also be provided with a second lens frame 70, having a substantially similar structure to first lens frame 22. Second lens frame 70 need not have the same structure as first lens frame 22, but will preferably have a second lens aperture 71, a second lens 72 and a second spacer member 73. Further, it is preferred second lens frame 70 be hingedly attached to helmet 10 via hinge mechanism 74, which may be substantially similar to hinge mechanism 23.

It is also preferred that lens assembly 20 be provided with a storage shroud 75, and that second lens frame be operable via second hinge mechanism 74, between an open position and a closed position. Storage shroud 75 extends from lens assembly 20, away from face portion 11. The "open position" of second lens frame 70 is understood to be away from observation aperture 16, and preferably is a position wherein second spacer member 73 is fitted within storage shroud 75 in a manner substantially similar to the fit between first spacer member 40 and shroud 21 as described above (FIG. 2). The "closed position" is understood to be when the second frame 70 is in juxtaposition with observation aperture 16, and the wearer of the helmet has a field of view through observation aperture 16 and through second lens 72 (FIG. 3).

In the "closed position," second spacer member 73 is preferably in contact with shroud 21, thereby effectively limiting movement of second lens frame 70 in a direction toward observation aperture 16. Of course, it is understood that such limitation may be accomplished by other methods, all within the scope of the present invention.

Second lens frame is held in the closed position by structures substantially similar to those employed with first lens frame 22. Preferably, these include clips 50 and/or magnetic elements 51.

It is still further preferred that second lens 72 be a lens employed in cutting procedures. As discussed above, complete blockage of light radiation emissions is not as essential during cutting operations as during welding. Thus, while second spacer member 73 does not contact shroud 21, thus ensuring blockage of light, this is not of a great concern when the second lens is used for cutting.

Thus it is to be appreciated by one skilled in the art, that a welder's safety helmet according to the present invention will ensure that all light radiation emissions are blocked except for the desired transmissions through the first lens 17. Further, the structures employed to hold the welding lens frames over the wearer's field of view are effectively protected from damage. Thus the invention disclosed herein and defined by the following claims accomplishes the objects of the present invention and otherwise constitutes an advantageous contribution to the art.

I claim:

1. A welder's helmet having a face portion with an observation aperture therein, the helmet comprising:
    a lens assembly disposed upon the face of the helmet, said lens assembly having a first shroud extending therefrom in a direction away from the face, said first shroud substantially surrounding the observation aperture;
    a first lens frame carrying a first lens, said first lens frame being connected via hinge means to the helmet and operable via said hinge means between an open position away from the observation aperture and a closed position in juxtaposition with the observation aperture;
    a spacer member substantially surrounding said first lens, said spacer member being in engagement with said first shroud when said lens frame is in said closed position, such that said engagement of said spacer member of said first lens frame with said first shroud when said first lens frame is in said closed position prevents light from traversing between said spacer member and said first shroud and past the face portion;
    a second lens assembly including a frame carrying a second lens, said second lens frame being connected via second hinge means to the helmet and operable via said second hinge means between an open position away from the observation aperture and a closed position in juxtaposition with the observation aperture, said second lens assembly further including a storage shroud extending therefrom and away from said face and a second spacer in engagement with said storage shroud when said second lens frame is in said open position; and
    means received within said first shroud for securing said first and second lens frames in said closed position.

2. A welder's helmet as in claim 1, wherein said means for securing said first lens frame in said closed position includes clip means.

3. A welder's helmet as in claim 1, wherein said means for securing said first lens frame in said closed position includes magnetic elements.

4. A welder's helmet as in claim 1, wherein said first lens is a welding lens and said second lens is a cutting lens.

5. A welder's helmet as in claim 1, further comprising a clear glass lens affixed to cover the observation aperture.

6. A welder's helmet as in claim 1, further comprising two clear glass lenses disposed on either side of said first lens.

7. A welder's helmet as in claim 12, wherein said clear glass lenses and said first lens are held in place on said first lens frame by a plurality of pressure fingers.

* * * * *